United States Patent
Li et al.

(10) Patent No.: US 9,669,392 B2
(45) Date of Patent: Jun. 6, 2017

(54) CATALYST FOR SELECTIVE HYDROGENATION OF DIENES, PREPARATION METHOD AND APPLICATION THEREOF

(71) Applicant: DALIAN INSTITUTE OF CHEMICAL PHYSICS, CHINESE ACADEMY OF SCIENCES, Dalian, Liaoning (CN)

(72) Inventors: Can Li, Dalian (CN); Zongxuan Jiang, Liaoning (CN); Yandie Chen, Liaoning (CN); Tiefeng Liu, Liaoning (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 187 days.

(21) Appl. No.: 14/419,433

(22) PCT Filed: Nov. 23, 2012

(86) PCT No.: PCT/CN2012/085114
§ 371 (c)(1),
(2) Date: Feb. 3, 2015

(87) PCT Pub. No.: WO2014/032366
PCT Pub. Date: Mar. 6, 2014

(65) Prior Publication Data
US 2015/0224481 A1 Aug. 13, 2015

(30) Foreign Application Priority Data
Aug. 30, 2012 (CN) .......................... 2012 1 0315165

(51) Int. Cl.
*B01J 21/02* (2006.01)
*B01J 21/04* (2006.01)
(Continued)

(52) U.S. Cl.
CPC ......... *B01J 23/8885* (2013.01); *B01J 23/002* (2013.01); *B01J 23/75* (2013.01);
(Continued)

(58) Field of Classification Search
CPC ... B01J 21/02; B01J 21/04; B01J 21/12; B01J 21/063; B01J 21/066; B01J 23/002;
(Continued)

(56) References Cited

U.S. PATENT DOCUMENTS 3,531,398 A * 9/1970 Adams ...................... B01J 23/85
  208/211
3,956,105 A * 5/1976 Conway ................... B01J 23/85
  208/111.3
(Continued)

FOREIGN PATENT DOCUMENTS

CN 1071443 A 4/1993
CN 1301591 A 7/2001
(Continued)

OTHER PUBLICATIONS

G.Alonso-Nunez et al., Applied Catalysis A: General 304 (2006)124-130.
(Continued)

*Primary Examiner* — Cam N. Nguyen
(74) *Attorney, Agent, or Firm* — Enshan Hong; VLP Law Group LLP

(57) ABSTRACT

A mixed metal oxide catalyst for selective hydrogenation of dienes comprising a Group VIII metal, a trivalent metal, a Group IA metal, a Group IVB metal, a Group IIB metal, two Group VIB metals and $SiO_2$—$Al_2O_3$ as balance. The catalyst comprises 10-40 wt % of Group VIII metal, 5-30 wt % of trivalent metal, 0.1-8 wt % of Group IA metal, 0.1-8 wt % of Group IVB metal, 0.1-30 wt % of Group IIB metal, 5-50 wt % of two Group VIB metals and 10-30 wt % of
(Continued)

$SiO_2$—$Al_2O_3$, based on the catalyst in terms of oxide, and has 150-300 m$^2$/g of specific surface area, 0.4-0.8 ml/g of pore volume.

13 Claims, 1 Drawing Sheet

(51) Int. Cl.

| | | |
|---|---|---|
| B01J 21/12 | (2006.01) | |
| B01J 21/06 | (2006.01) | |
| B01J 23/00 | (2006.01) | |
| B01J 23/06 | (2006.01) | |
| B01J 23/24 | (2006.01) | |
| B01J 23/75 | (2006.01) | |
| B01J 23/755 | (2006.01) | |
| B01J 23/80 | (2006.01) | |
| B01J 23/85 | (2006.01) | |
| B01J 23/888 | (2006.01) | |
| B01J 35/00 | (2006.01) | |
| B01J 35/02 | (2006.01) | |
| B01J 35/10 | (2006.01) | |
| B01J 37/00 | (2006.01) | |
| B01J 37/02 | (2006.01) | |
| B01J 37/03 | (2006.01) | |
| B01J 37/20 | (2006.01) | |
| C07C 7/163 | (2006.01) | |
| B01J 29/04 | (2006.01) | |
| C10G 45/38 | (2006.01) | |

(52) U.S. Cl.
CPC ........... *B01J 23/755* (2013.01); *B01J 23/888* (2013.01); *B01J 29/049* (2013.01); *B01J 35/002* (2013.01); *B01J 35/026* (2013.01); *B01J 35/1019* (2013.01); *B01J 35/1038* (2013.01); *B01J 35/1042* (2013.01); *B01J 37/0009* (2013.01); *B01J 37/0201* (2013.01); *B01J 37/03* (2013.01); *B01J 37/033* (2013.01); *B01J 37/20* (2013.01); *C07C 7/163* (2013.01); *C10G 45/38* (2013.01); *B01J 2523/00* (2013.01)

(58) Field of Classification Search
CPC ... B01J 23/06; B01J 23/24; B01J 23/75; B01J 23/755; B01J 23/80; B01J 23/85; B01J 23/888; B01J 23/8885; B01J 37/0009; B01J 37/0201; B01J 37/03; B01J 37/033; B01J 37/20; B01J 35/002; B01J 35/026; B01J 35/1019; B01J 35/1038; B01J 35/1042; C07C 7/163
See application file for complete search history.

(56) References Cited

U.S. PATENT DOCUMENTS

| | | | | | |
|---|---|---|---|---|---|
| 3,969,274 | A | * | 7/1976 | Frampton | B01D 53/86 502/213 |
| 4,098,683 | A | * | 7/1978 | Conway | C10G 49/04 208/143 |
| 4,102,822 | A | * | 7/1978 | Mulaskey | B01J 23/84 208/136 |
| 4,115,248 | A | * | 9/1978 | Mulaskey | B01J 23/84 208/108 |
| 4,210,525 | A | * | 7/1980 | Peters | B01J 23/85 208/212 |
| 4,394,302 | A | * | 7/1983 | Miller | B01J 23/04 208/216 R |
| 4,460,707 | A | * | 7/1984 | Simpson | B01J 35/10 208/216 PP |
| 4,526,675 | A | * | 7/1985 | Mahoney | B01J 23/24 208/106 |
| 4,548,710 | A | * | 10/1985 | Simpson | C10G 49/04 208/216 PP |
| 6,084,140 | A | | 7/2000 | Kitamura et al. | |
| 6,156,695 | A | | 12/2000 | Soled et al. | |
| 6,255,548 | B1 | | 7/2001 | Didillon et al. | |
| 6,299,760 | B1 | | 10/2001 | Soled et al. | |
| 6,388,162 | B1 | | 5/2002 | Himelfarb et al. | |
| 6,712,955 | B1 | | 3/2004 | Hou et al. | |
| 6,758,963 | B1 | | 7/2004 | Hantzer et al. | |
| 6,783,663 | B1 | | 8/2004 | Riley et al. | |
| 7,229,548 | B2 | * | 6/2007 | Riley | B01J 23/85 208/113 |
| 2012/0016171 | A1 | * | 1/2012 | Kustov | B01J 23/002 585/662 |
| 2013/0338413 | A1 | | 12/2013 | Fecant | |

FOREIGN PATENT DOCUMENTS

| | | |
|---|---|---|
| CN | 1339985 A | 3/2002 |
| CN | 1221638 C | 12/2004 |
| CN | 1676580 A | 10/2005 |
| CN | 1708684 A | 12/2005 |
| CN | 1272103 C | 8/2006 |
| CN | 1286951 C | 11/2006 |
| CN | 1291785 C | 12/2006 |
| CN | 1317365 C | 5/2007 |
| CN | 1317366 C | 5/2007 |
| CN | 100338190 C | 9/2007 |
| CN | 100566827 C | 4/2008 |
| CN | 101153228 A | 4/2008 |
| CN | 101544904 A | 9/2009 |
| CN | 101619236 A | 1/2010 |
| CN | 101628843 A | 1/2010 |
| CN | 101733120 A | 6/2010 |
| CN | 101844081 A | 9/2010 |
| CN | 102451715 A | 5/2012 |
| CN | 102600909 A | 7/2012 |
| FR | 2970881 A1 | 8/2012 |

OTHER PUBLICATIONS

G.Alonso-Nunez et al., Applied Catalysis A: General 302 (2006)177-184.

G.Alonso-Nunez et al., Catalysis Letters 99(2005) 65-71.

Peng Liu etc., Epoxidation of Allylic Alcohols on Self-Assembled Polyoxometalates Hosted in Layered Double Hydroxides with Aqueous H2O2 as Oxidant, Journal of Catalysis, Feb. 15, 2009 vol. 262, No. 1, pp. 159-168, ISSN 0021-9517.

* cited by examiner

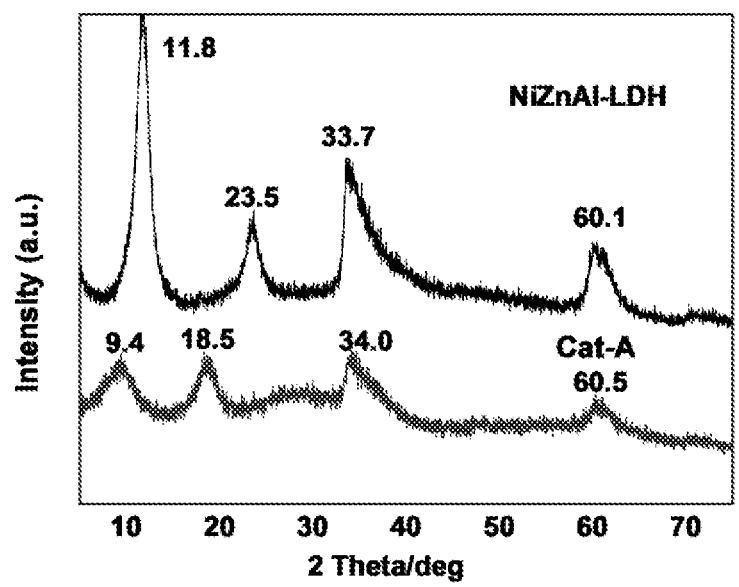

CATALYST FOR SELECTIVE HYDROGENATION OF DIENES, PREPARATION METHOD AND APPLICATION THEREOF

PRIORITY CLAIM

This is a U.S. national stage of application No. PCT/CN2012/085114, filed on Nov. 23, 2012, which claims priority from Chinese Patent Application No. 201210315165.9 filed Aug. 30, 2012, the entire content of which is hereby incorporated by reference.

FIELD OF THE INVENTION

The present invention relates to selective hydrogenation of diolefin, specifically involves a diolefin selective hydrogenation catalyst, preparation method and use thereof. The catalyst possesses layered structure, showing ultra-high selectivity and hydrogenation activity of diolefin.

BACKGROUND OF THE INVENTION

Diolefin are widely present in FCC gasoline, pyrolysis gasoline and olefin-rich feed-stock. Diolefin are highly reactive and easy to form polymer, gum and coke precursors itself or with other olefins. Therefore, in order to avoid diolefin coking on catalysts and affecting lifetime, it is necessary to remove diolefin before treating gasoline and olefin-rich feedstock.

At present, selective hydrogenation is the main route to remove diolefin in refineries. Namely, diolefin are removed by selective hydrogenation over hydrogenation catalysts to achieve the purpose of removal of diolefin. There are three kinds of selective hydrogenation catalysts for removing diolefin. The first are catalysts loading noble metal (mainly Pd), such as catalysts disclosed in patents U.S. Pat. No. 6,388,612, U.S. Pat. No. 6,255,548, U.S. Pat. No. 6,084,140, CN 101628843 and CN 1071443A, which provided a method to remove diolefin in olefin-rich feed-stock using Pd/α-Al2O3. The patents also pointed that some other metals such as Ag, Cu and Co could also be added to improve the selectivity of diolefin. The Pd content was in the range of 0.05-0.2 wt %, preferably Pd content was 0.2 wt %, and the preferable reaction temperature was 26-49° C. This type of catalysts exhibits high efficiency on feed-stock with low or no toxicants (e.g., S and As). However, the catalysts are easy to be inactive when treating FCC gasoline, pyrolysis gasoline and olefin-rich feed-stock with high toxicants as above mentioned, and so forth, and then the life of the catalysts are seriously affected. Besides, the price of Pd is also expensive.

The second are Ni-based supported or amorphous state Ni-based catalysts, such as catalysts disclosed in patents CN1221638C, CN99120660.6, and CN100566827C. These patents disclosed a method to remove diolefin in olefin-rich feed-stock using Ni-based supported or amorphous state Ni-based catalysts, where the non-oxidizing porous supports are composed of molecular sieves, active carbon, inorganic oxides and so on. The process of removing diolefin has following features: reaction temperature of 40-70° C., pressure of 1.0-3.0 MPa, $H_2$/oil ratio of 100-700 $Ncm^3/cm^3$, and LHSV of 0.5-4.0 $h^{-1}$. The catalysts have high efficiency on feed-stock with low or no toxicants (e.g. S and As). However, the Ni-based catalysts are easy to be poisoned and inactive when treating FCC gasoline, pyrolysis gasoline and olefin-rich feed-stock with high toxicants (e.g. S and As) as above mentioned and so forth, and then the life of the catalysts are seriously affected.

The third are transition metal sulfides supported catalysts. Chinese patents CN1676580A, CN101619236A, CN100338190C, CN1317366C, CN1317365C, CN1286951C, CN1291785C and CN1272103C had published a method to selectively remove diolefin in distillate using catalysts which were composed of Ni(Co)—Mo(W)—K/$Al_2O_3$ and alkali metal (e.g. K). Prior to reaction, it is necessary to sulfide catalysts to form sulfided active species. The operating conditions of diolefin selective hydrogenation have following features: reaction temperature of 160-300° C., preferably 200-260° C.; 1.0-6.0 MPa of $H_2$ pressure, preferably 1.2-4.0 MPa; LHSV of 2.0-30.0 $h^{-1}$, preferably 5.0-20.0 $h^{-1}$; and $H_2$/oil ratio of 50-600 $Ncm^3/cm^3$, preferably 100-400 $Ncm^3/cm^3$. Compared with the two mentioned kinds of catalysts, the third catalysts exhibit high selectivity and good S, As anti-poisoning ability, and existence of alkalis could inhibit carbon deposition on catalyst surface. However, this type of catalyst also has insuperable defects of its own. Due to limited active metals loaded, the catalysts still require high temperature and show low reactivity. Meanwhile, high temperature also accelerates coking, catalysts become inactive easily, and the lifetime of catalysts will decrease greatly, and greatly affects the long-term stable operation of the device. Therefore, it is necessary to develop inexpensive catalysts with high activity and selectivity to remove diolefin under relatively low temperature, while possessing strong S, As anti-poisoning ability and high metal contents, but economic compared with noble metal.

U.S. Pat. Nos. 6,299,760, 6,156,695, 6,783,663, 6,712,955, and 6,758,963 have disclosed a new tri-metallic NiMoW catalyst with high metal content, its preparation and application in ultra-deep hydrodesulfurization of diesel. The HDS activity of the NiMoW catalyst is at least about 3 times of other conventional supported catalysts. The NiMoW catalyst was prepared using ammonia as a cheating agent to react with $Ni^{2+}$. Via slow heating, the $Ni^{2+}$ complex in solution of Mo and W would decompose and then the NiMoW precursor was obtained. Sulfided NiMoW catalyst was formed after calcination and sulfidation. The disadvantage of this method is that concentrated ammonia is a pollutant, and the complex of $Ni^{2+}$ with ammonia was too stable to release ammonia, leaving complex ions of $Ni^{2+}$ with ammonia in the liquid remnants, and leading to large quantities of waste water that cannot be discharged. The prepared catalysts in these patents possess low surface area (<120 $m^2/g$) and volume (<0.2 ml/g), while in HDS reaction of diesel these catalysts shown high HDS activity only under conditions of high pressure (>6 MPa) and $H_2$/oil ratio (>500 $Ncm^3/cm^3$). But when treating olefin-rich feed-stock, the catalysts would lose activity quickly, and this limited the industrial application.

G. Alonso-Nunez et al. in their work (Applied Catalysis A: General 304 (2006)124-130; Applied Catalysis A: General 302 (2006)177-184) and Catalysis Letters 99(2005)65-71)) reported several preparation methods of NiMoW catalysts via different raw materials and various curing agents. The catalysts they prepared had special flaked shape, but the synthesis method was so complex that the steps were also complex and the raw materials were expensive, leading to high costs of catalysts. Moreover, it is also difficult to have a extrusion molding for the sulfided catalyst powder, which limited the industrial application.

Chinese Patent Application Publication No. CN 1339985A also developed a route to synthesize NiMoW catalyst, in which via reaction of Mo, W salts and basic nickel carbonate in water the solid precursor was obtained, and then sulfided the solid precursor. During the procedure at least part of the metal components exists in solid form. Due to using solid Ni source, which is insoluble in water and the essence of synthesis reactions is an ion-exchanged reaction, it is not easy to prepare a catalyst with a small size. The activity of catalyst made no difference from the conventional alumina supported catalysts. CN 101153228A, CN 101544904A and CN 101733120A disclosed a NiMoW trimetallic bulk catalyst, its preparation and use in ultra-deep hydrodesulfurization of diesel, too. Though the bulk catalyst exhibited ultra-high HDS activity in diesel ultra-deep hydrodesulfurization reaction of diesel, it could not be used in removing diolefin from olefin-rich feed-stock, because of low surface area and volume (low carbon capacity). The diolefin declined coking on the catalyst, which would result in a short lifetime of the catalyst, and the diolefin removal could not meet the demand for industrial application.

Based on the existing reports, there are several drawbacks for diolefin removal catalysts as follows: (1) Pd-based and Ni-based supported catalysts with poor S, As anti-poisoning ability and short lifetime, could not treat feedstock containing S and As effectively; (2) the price of Pd-based catalysts is expensive; (3) conventional transition metal sulfided catalysts show low activity, require high temperature and become inactive easily. Therefore, it is necessary to develop inexpensive catalysts to remove diolefin with high activity and selectivity under relatively low temperature, while still possess strong S, As anti-poisoning ability and high metal contents, and economic compared with noble metal.

SUMMARY OF THE INVENTION

The present invention provides a catalyst to remove diolefin. The invention also provides a method of preparation of the catalyst, To achieve said purpose, the present invention provides a catalyst for selective hydrogenation of diolefin. The catalyst is a mixed metal oxides catalyst, and comprises one trivalent metal, one Group IA metal, one Group IIB metal, one Group IVB metal, one Group VIII metal, two Group VIB metals and balance volume of silica and/or alumina. It is characterized in, on oxide basis, it comprises 10-40 wt % of Group VIII metals, 5-30 wt % of trivalent metals, 0.1-8 wt % of Group IA metal, 0.1-8 wt % of Group IVB metal, 0.1-30 wt % of Group JIB metal, 5-50 wt % of two Group VIB metals, and 10-30 wt % of $SiO_2$—$Al_2O_3$. The surface area of catalyst is 150-300 m$^2$/g and pore volume is 0.4-0.8 ml/g.

In a preferable embodiment of the invention, the trivalent metal is selected from Cr or Al, Group IA metal is selected from Na or K, Group IVB metal is selected from Ti or Zr, Group IIB metal is selected from Zn, Group VIII metals are selected from nickel or cobalt, and two Group VIB metals are selected from molybdenum and tungsten.

In another preferable embodiment of the invention, Group VIB metals are selected from Mo and W, Group IIB metal is selected from Zn, Group IA metal is selected from K, Group IVB metal is selected from Ti, Group VIII metal is selected from Ni and trivalent metal is selected from Al.

This invention is a catalyst that is able to remove diolefin with high activity and selectivity under relatively low temperature, while still possess strong S, As anti-poisoning ability and high metal contents, and economic compared with noble metal.

In a preferable embodiment of the invention, a method to prepare the aforementioned catalyst is provided, comprising the following steps:

a) Mixing Group VIII metal soluble salt, Group IIB metal soluble salt and one trivalent metal soluble salt and then dissolving in water to obtain a water solution; adding aqueous solution of basic precipitant containing Group IA metal to the mentioned solution to form a catalyst precipitate, then a layered double hydroxide catalyst precursor was obtained;

b) Combining the slurry of mentioned layered double hydroxide catalyst precursor and polar solvent containing at least two Group VIB metals soluble salts together for ion-exchanged reaction, filtering the catalyst precursor, washing, drying and calcining catalyst precursor, and a mixture of oxide metals was obtained, comprising one Group VIII metal, one trivalent metal, one Group IA metal, one Group IIB metal, two Group VIB metals.

c) Grinding the mixture of oxide metals into powder with a size at least lager than 100 mesh, then mix the powder with a binder containing Group IVB oxide metals and a mixture of $SiO_2$ and/or $Al_2O_3$ together for kneading and extrusion molding. Via drying and calcination, the mixed oxide metal catalyst consisted of one Group IVB metal, one Group IA metal, one trivalent metal, one Group IIB metal, one Group VIII metal, two Group VIB metals and a certain amount of $SiO_2$—$Al_2O_3$ was prepared. In a preferable embodiment of the invention, the concentration of solution of Group VIII metal soluble salt lies in the range of from 0.01 to 0.3 M, the concentration of solution of trivalent metal soluble salt lies in the range of from 0.01 to 0.3 M, the concentration of solution of Group IIB metal soluble salt lies in the range of from 0.01 to 0.3 M, the concentration of aqueous solution of basic precipitant containing Group IA metal lies in the range of from 0.1 to 1.5 M, the concentration of layered double hydroxide catalyst precursor is in the range of from 0.01 to 0.9 M, and the concentration of at least two Group VIB metal soluble salt solving in polar solvent is in the range of from 0.01 to 0.2 M.

In another preferable embodiment of the invention, said precipitation reaction in step a) is performing in the range of from 50 to 150° C. about from 10 to 25 h; the ion-exchanged reaction mentioned in step b) is performing in the range of from 50 to 150° C. about from 4 to 10 h.

In another preferable embodiment of the invention, the basic precipitant mentioned in step a) is selected from sodium hydroxide, potassium hydroxide, sodium carbonate, potassium carbonate, and mixtures of any two or more thereof; the pH of ion-exchanged reaction system mentioned in step b) is in the range of from 1 to 11.

In another preferable embodiment of the invention, the Group VIII metal soluble salt is selected from nickel nitrate, nickel acetate, nickel sulfate, nickel chloride or cobalt nitrate, cobalt acetate, cobalt sulfate, or cobalt chloride; the trivalent metal soluble salt is selected from aluminium nitrate, aluminium acetate, aluminium chloride, chromium nitrate, chromium acetate, chromium chloride, cobalt nitrate or cobalt chloride.

In another preferable embodiment of the invention, a mixture of at least two Group VIB metal soluble salts comprise one selected from ammonium molybdate or sodium molybdate and the other selected from ammonium tungstate, ammonium meta-tungstate, or sodium tungstate.

In another preferable embodiment of the invention, the invention provides a use of aforementioned catalyst in the selective hydrogenation of diolefin.

In a preferable embodiment of the invention, in the selective hydrogenation of diolefin reaction, temperatures lie in the range of from 30 to 220° C., hydrogen partial pressures are in the range of from 0.1 to 10 MPa, H$_2$/oil ratio is in the range of from 10 to 300 Nm³/m³, and typical liquid hourly space velocity is in the range of from 0.1 to 10 h⁻¹.

In another preferable embodiment of the invention, the process of pretreating the catalysts before carrying out the selective hydrogenation of diolefin reaction includes: a) calcining under air atmosphere at temperature from 350 to 550° C.; b) grinding, kneading, and extrusion molding; c) in a fixed-bed reactor, carrying out sulfidation in-situ using mixture of sulfur containing material and hydrogen at temperature in the range of from 250 to 400° C.

In a preferable embodiment of the invention, sulfur containing material is selected from hydrogen sulfide, carbon disulfide or dimethyl disulfide.

Compared to prior art, the present invention has several advantages as follows:

1. The synthesis process is easy to operate, catalyst is green to environment and can be produced in commercial process.
2. The synthesized catalysts possess high active materials, large surface area (>150 m²/g) and volume (>0.4 ml/g).
3. The price of catalysts in the invention is cheap due to lack of noble metal.
4. Under mild conditions (80° C., 1.0 MPa of $H_2$ pressure, LHSV of 2 h⁻¹, and $H_2$/oil ratio of 50 Ncm³/cm³.), used in the selective hydrogenation of diolefin reaction of olefin-rich feed-stock, the catalysts can reduce diene value (in the form of dienes) of FCC gasoline from 0.72 g$I_2$/100 g oil to less than 0.1 g$I_2$/100 g oil, exhibiting significant selective hydrogenation activity. And the catalysts in compared examples could only reduce diene value to about 0.5 g$I_2$/100 g under the same conditions.
5. The catalysts exhibit strong S and As anti-poisoning and strong anti-coking ability. A lifetime experiment of 500 h shows that the catalyst in the invention could maintain high activity at low temperature (<100° C.).

BRIEF DESCRIPTION OF THE DRAWINGS

FIG. 1 shows the X-ray diffraction patterns of NiZnAl-LDH precursor and Cat-A catalyst prepared in Example 1.

DETAILED DESCRIPTION OF THE INVENTION

In one hand, this invention provides a catalyst for selective hydrogenation of diolefin. The catalyst is an mixed metal oxides catalyst, and comprises one Group IA metal, one Group IIB metal, one Group IVB metal, one Group VIII metal, two Group VIB metals, and balance volume of silica and/or alumina. It is characterized in, on oxide basis, it comprises 10-40 wt % of Group VIII metals, 5-30 wt % of trivalent metals, 0.1-8 wt % of Group IA metal, 0.1-8 wt % of Group IVB metal, 0.1-30 wt % of Group IIB metal, 5-50 wt % of two Group VIB metals, and 10-30 wt % of $SiO_2$—$Al_2O_3$. The surface area of catalyst is 150-300 m²/g and pore volume is 0.4-0.8 ml/g.

In a preferable embodiment of the invention, the trivalent metal is selected from Cr or Al, Group IA metal is selected from Na or K, Group IVB metal is selected from Ti or Zr, Group IIB metal is selected from Zn, Group VIII metals are selected from nickel or cobalt, and Group VIB metal is selected from molybdenum or tungsten.

In another preferable embodiment of the invention, Group VIB metals are selected from Mo and W, Group IIB metal is selected from Zn, Group IA metal is selected from K, Group IVB metal is selected from Ti, Group VIII metal is selected from Ni and trivalent metal is selected from Al.

On the other hand, this invention also provides a method for preparation of the catalyst comprising the following steps:

a) Dissolving Group VIII metal soluble salt, Group IIB metal soluble salt and one trivalent metal soluble salt in water, adding aqueous solution of basic precipitant containing Group IA metal to mentioned solution to form a catalyst precipitate, then a layered double hydroxide catalyst precursor was obtained.

b) Combining the slurry of mentioned layered double hydroxide catalyst precursor and polar solvent containing at least two Group VIB metals together for ion-exchanged reaction, filtering the catalyst precursor, washing, drying and calcining catalyst precursor, and a mixture of oxide metals was obtained, comprising one Group VIII metal, one trivalent metal, one Group IA metal, one Group IIB metal, two Group VIB metals.

c) Grinding the mixture into powder with a size at least lager than 100 mesh, then mix the powder with a binder containing Group IVB oxide metals and a mixture of $SiO_2$ and/or $Al_2O_3$ together for kneading, and extrusion molding. Via drying and calcination, the mixed oxide metal catalyst consisted of one Group IVB metal, one Group IA metal, one trivalent metal, one Group IIB metal, one Group VIB metal, two Group VIII metals and a certain amount of $SiO_2$—$Al_2O_3$ was prepared.

In a preferable embodiment of the invention, the concentration of solution of Group VIII metal soluble salt lies in the range of from 0.01 to 0.3 M, the concentration of solution of trivalent metal soluble salt lies in the range of from 0.01 to 0.3 M, the concentration of solution of Group IIB metal soluble salt lies in the range of from 0.01 to 0.3 M, the concentration of aqueous solution of basic precipitant containing Group IA metal precursors lies in the range of from 0.1 to 1.5 M, the concentration of layered double hydroxide catalyst precursor is in the range of from 0.01 to 0.9 M, and the concentration of at least two Group VIB metal soluble salt solving in polar solvent is in the range of from 0.01 to 0.2 M.

In another preferable embodiment of the invention, the precipitation reaction temperature mentioned in step a) is in the range of from 50 to 150° C. about from 10 to 25 h; the ion-exchanged reaction temperature mentioned in step b) is in the range of from 50 to 150° C. about from 4 to 10 h;

In another preferable embodiment of the invention, the basic precipitant mentioned in step a) is selected from sodium hydroxide, potassium hydroxide, sodium carbonate, potassium carbonate, and mixtures of any two or more thereof; the pH of ion-exchanged reaction system mentioned in step b) is in the range of from 1 to 11.

In another preferable embodiment of the invention, the Group VIII metal soluble salt is selected from nickel nitrate, nickel acetate, nickel sulfate, nickel chloride or cobalt nitrate, cobalt acetate, cobalt sulfate, or cobalt chloride; the trivalent metal soluble salt is selected from aluminium nitrate, aluminium acetate, aluminium chloride, chromium nitrate, chromium acetate, chromium chloride, cobalt nitrate or cobalt chloride.

In another preferable embodiment of the invention, a mixture of at least two Group VIB metal soluble salts comprise one selected from ammonium molybdate or sodium molybdate and the other selected from ammonium tungstate, ammonium meta-tungstate, or sodium tungstate.

In another preferable embodiment of the invention, the invention provides a use of aforementioned catalyst in the selective hydrogenation of diolefin.

In a preferable embodiment of the invention, the process of use of the invention is operated under suitable reaction conditions. Temperatures lie in the range of from 30 to 220° C., hydrogen partial pressures are in the range of from 0.1 to 10 MPa, $H_2$/oil ratio is in the range of from 10 to 300 $Nm^3/m^3$, and typical liquid hourly space velocity is in the range of from 0.1 to 10 $h^{-1}$.

In another preferable embodiment of the invention, the process of pretreating the catalysts before the selective hydrogenation of diolefin reaction includes:

a) Calcining under air atmosphere at temperature from 350 to 550° C.;

b) Grinding, kneading, and extrusion molding;

c) In a fixed-bed reactor, carrying out sulfidation in-situ using mixture of sulfur containing material and hydrogen at temperature in the range of from 250 to 400° C.

In a preferable embodiment of the invention, sulfur containing material is selected from hydrogen sulfide, carbon disulfide or dimethyl disulfide.

FIG. 1 shows the X-ray diffraction patterns of NiZnAl-LDH precursor and Cat-A catalyst prepared in Example 1. It can be found that in XRD pattern of NiZnAlK-LDH, there are four peaks with strong intensity at 2θ=11.8°, 23.5°, 33.7° and 60.1°, respectively. After ion-exchanged reaction of LDH with Mo and W salts, four wide peaks at 2θ=9.4°, 18.5°, 34.0° and 60.5° are detected. The intensity and position of these peaks make difference with that in patents CN101733120A and U.S. Pat. No. 6,299,760, suggesting that the structure of catalysts in this invention is different from that in other mentioned patents.

EXAMPLES

The following examples illustrate the present invention, but they don't limit the invention scope of claim. For example, according to experiment results we can prepare a mixed metal oxides catalyst composed one trivalent metal, one Group IA metal, one Group JIB metal, one Group IVB metal, one Group VIII metal, two Group VIB metals and certain amount of $SiO_2$—$Al_2O_3$, wherein the trivalent metal suitably is selected from Cr or Al, Group IA metal is selected from Na or K, Group IVB metal is selected from Ti or Zr, Group JIB metal is selected from Zn, Group VIII metals are selected from nickel or cobalt, and two Group VIB metals are selected from molybdenum and tungsten. Here this invention illustrates examples of NiZnAlKTiMoW/$SiO_2$—$Al_2O_3$ catalyst, but that doesn't mean another metals cannot be used.

Example 1

Preparation of NiZnAlKTiMoW/$SiO_2$—$Al_2O_3$ Catalyst a. A certain amount of nickel nitrate, zinc nitrate and aluminium nitrate (0.1 mol $Ni^{2+}$, 0.1 mol $Zn^{2+}$, 0.05 mol $Al^{3+}$) were dissolved in 0.2 L of deionized water, aqueous solution of 0.2 M $K^+$ (a mixture of 0.1M KOH and 0.05 M $K_2CO_3$) was added to the above solution with constant stirring to maintain the pH=12, and then the solution was heated to reaction temperature of 80° C. to form a aqua solution. Keeping the reflux reaction at 80° C. for 25 h to obtain aqua precipitate, filtering the precipitate and washing, then the catalyst precursor was obtained. The aqua catalyst precursor was dispersed into 0.2 L of deionized water to form slurry (a).

b. A certain amount of ammonium molybdate and ammonium meta-tungstate (0.01 mol $Mo^{6+}$, 0.01 mol $W^{6+}$) were dissolved in 0.35 L of deionized water, and the resulting molybdate/tungstate solution was heated to reaction temperature with continuing stirring to form a colorless solution. The above slurry (a) containing 0.03 mol $Ni^{2+}$, 0.03 mol $Zn^{2+}$, 0.015 mol $Al^{3+}$ was heated to reaction temperature of 80° C. and was added to the resulting colorless molybdate/tungstate solution to form a aqua solution. The aqua solution was kept refluxing at 80° C. for 5 h to get yellow-green precipitate. The sepia NiZnAlKTiMoW/$SiO_2$—$Al_2O_3$ catalyst was prepared by filtering, washing and drying the yellow-green precipitate at 120° C. for 12 h and calcined at 420° C. for 4 h.

c. The NiZnAlKTiMoW catalyst was grinded into powder with a size 160 mesh, then mixing the powder with binder of $SiO_2$—$Al_2O_3$ containing Ti together for kneading, and extrusion molding into trifoliumed shape (φ2.0). Drying the extruded catalyst at 120° C. for 12 h and the catalyst is calcined at 420° C. for 4 h to obtain NiZnAlKTiMoW/$SiO_2$—$Al_2O_3$. Via element analysis (XRF), it contains 6.9% NiO, 18.4% ZnO, 10.9% $MoO_3$, 17.5% $WO_3$, 5.8% $Al_2O_3$, 2.7% $TiO_2$, 2.8% $K_2O$ and 25.0% $SiO_2$—$Al_2O_3$ ($SiO_2$ is 96% in $SiO_2$—$Al_2O_3$). Before selective hydrogenation of diolefin reaction, the catalyst was pre-sulfided in 10% $H_2S$/$H_2$ atmosphere at 400° C. for 2 h, and the flow rate of 10% $H_2S/H_2$ gas was 60 mL/min.

The sepia catalyst of the example is marked Cat-A, whose XRD pattern is listed in FIG. 1.

Example 2

Nickel nitrate (0.09 mol $Ni^{2+}$) and aluminium nitrate (0.03 mol $Al^{3+}$) were used instead of nickel nitrate (0.1 mol $Ni^{2+}$) and aluminium nitrate (0.05 mol $Al^{3+}$) of Example 1, the catalyst was prepared following the precipitation route described in Example 1. The catalyst of this example is marked as Cat-B whose morphology is similar to Cat-A. Via XRF, it contains 36.3% NiO, 13.2% ZnO, 7.8% $MoO_3$, 12.5% $WO_3$, 8.3% $Al_2O_3$, 2.0% $TiO_2$, 2.0% $K_2O$ and 17.9% $SiO_2$—$Al_2O_3$.

Example 3

Nickel nitrate (0.03 mol $Ni^{2+}$) and aluminium nitrate (0.09 mol $Al^{3+}$) were used instead of nickel nitrate (0.1 mol $Ni^{2+}$) and aluminium nitrate (0.05 mol $Al^{3+}$) of Example 1, the catalyst was prepared following the precipitation route described in Example 1. The catalyst of this example is marked Cat-C. Via XRF, it contains 13.1% NiO, 14.3% ZnO, 8.4% $MoO_3$, 13.6% $WO_3$, 26.8% $Al_2O_3$, 2.2% $TiO_2$, 2.2% $K_2O$ and 19.4% $SiO_2$—$Al_2O_3$.

Example 4

Except using ammonium molybdate and ammonium meta-tungstate (0.01 mol $Mo^{6+}$, 0.03 mol $W^{6+}$) instead of ammonium molybdate and ammonium meta-tungstate (0.01 mol $Mo^{6+}$, 0.01 mol $W^{6+}$) of Example 1, the catalyst was prepared following the precipitation route described in Example 1. The catalyst of this example is marked Cat-D. Via XRF, it contains 12.5% NiO, 13.6% ZnO, 8.0% $MoO_3$, 38.9% $WO_3$, 4.3% $Al_2O_3$, 2.1% $TiO_2$, 2.1% $K_2O$ and 18.5% $SiO_2$—$Al_2O_3$.

Example 5

Except using ammonium molybdate and ammonium meta-tungstate (0.03 mol $Mo^{6+}$, 0.01 mol $W^{6+}$) instead of ammonium molybdate and ammonium meta-tungstate (0.01 mol $Mo^{6+}$, 0.01 mol $W^{6+}$) of Example 1, the catalyst was prepared following the precipitation route described in Example 1. The catalyst of this example is marked Cat-E. Via XRF, it contains 13.9% NiO, 15.1% ZnO, 26.8% $MoO_3$, 14.4% $WO_3$, 4.7% $Al_2O_3$, 2.3% $TiO_2$, 2.3% $K_2O$ and 20.5% $SiO_2$—$Al_2O_3$.

Example 6

Except using part of home-made slurry which contains 0.08 mol $Ni^{2+}$ instead of part of home-made slurry of Example 1, the catalyst was prepared following the precipitation route described in Example 1. The catalyst of this example is marked Cat-F. Via XRF, it contains 35.2% NiO, 14.4% ZnO, 8.5% $MoO_3$, 13.6% $WO_3$, 4.5% $Al_2O_3$, 2.2% $TiO_2$, 2.2% $K_2O$ and 19.4% $SiO_2$—$Al_2O_3$.

Example 7

Except using ammonium molybdate and ammonium meta-tungstate (0.02 mol $Mo^{6+}$, 0.02 mol $W^{6+}$) instead of ammonium molybdate and ammonium meta-tungstate (0.01 mol $Mo^{6+}$, 0.01 mol $W^{6+}$) of Example 1, and using part of home-made slurry which contains 0.04 mol $Ni^2$ instead of part of home-made slurry of Example 1, the catalyst was prepared following the precipitation route described in Example 1. The catalyst of this example is marked Cat-G. Via XRF, it contains 16.8% NiO, 13.7% ZnO, 16.2% $MoO_3$, 26.2% $WO_3$, 4.3% $Al_2O$, 2.1% TiO, 2.1% $K_2O$ and 18.6% $SiO_2$—$Al_2O_3$.

Example 8

Except performing reaction at 50° C. for 10 h instead of at 80° C. for 25 h at step a), then the catalyst was prepared following the precipitation route described in Example 1. The catalyst of this example is marked Cat-H. Via XRF, it contains 16.4% NiO, 18.9% ZnO, 10.3% $MoO_3$, 18.1% $WO_3$, 5.6% $Al_2O_3$, 2.9% $TiO_2$, 2.4% $K_2O$ and 25.4% $SiO_2$—$Al_2O_3$.

Example 9

Except performing reaction at 50° C. for 25 h instead of at 80° C. for 25 h at step a), then the catalyst was prepared following the precipitation route described in Example 1. The catalyst of this example is marked Cat-I. Via XRF, it contains 16.6% NiO, 18.7% ZnO, 10.8% $MoO_3$, 17.6% $WO_3$, 5.8% $Al_2O_3$, 2.7% $TiO_2$, 2.7% $K_2O$ and 25.0% $SiO_2$—$Al_2O_3$.

Example 10

Except performing reaction at 150° C. for 10 h instead of at 80° C. for 25 h at step a), then the catalyst was prepared following the precipitation route described in Example 1. The catalyst of this example is marked Cat-J. Via XRF, it contains 16.8% NiO, 18.5% ZnO, 10.2% $MoO_3$, 18.2% $WO_3$, 5.2% $Al_2O_3$, 3.0% $TiO_2$, 3.0% $K_2O$ and 25.0% $SiO_2$—$Al_2O_3$.

Example 11

Except performing reaction at 150° C. for 25 h instead of at 80° C. for 25 h at step a), then the catalyst was prepared following the precipitation route described in Example 1. The catalyst of this example is marked Cat-K. Via XRF, it contains 17.8% NiO, 16.5% ZnO, 11.2% $MoO_3$, 17.2% $WO_3$, 5.2% $Al_2O_3$, 3.0% $TiO_2$, 3.0% $K_2O$ and 25.0% $SiO_2$—$Al_2O_3$.

Example 12

Except performing reaction at 50° C. for 4 h instead of at 80° C. for 5 h at step b), then the catalyst was prepared following the precipitation route described in Example 1. The catalyst of this example is marked Cat-L. Via XRF, it contains 17.6% NiO, 16.7% ZnO, 11.0% $MoO_3$, 17.4% $WO_3$, 5.2% $Al_2O_3$, 3.0% $TiO_2$, 3.0% $K_2O$ and 25.0% $SiO_2$—$Al_2O_3$.

Example 13

Except performing reaction at 50° C. for 10 h instead of at 80° C. for 5 h at step b), then the catalyst was prepared following the precipitation route described in Example 1. The catalyst of this example is marked Cat-M. Via XRF, it contains 15.6% NiO, 17.7% ZnO, 12.0% $MoO_3$, 16.4% $WO_3$, 6.2% $Al_2O_3$, 3.0% $TiO_2$, 3.0% $K_2O$ and 25.0% $SiO_2$—$Al_2O_3$.

Example 14

Except performing reaction at 150° C. for 4 h instead of at 80° C. for 5 h at step b), then the catalyst was prepared following the precipitation route described in Example 1. The catalyst of this example is marked Cat-N. Via XRF, it contains 15.5% NiO, 17.8% ZnO, 11.0% $MoO_3$, 17.4% $WO_3$, 5.2% $Al_2O_3$, 3.0% $TiO_2$, 3.0% $K_2O$ and 26.0% $SiO_2$—$Al_2O_3$.

Example 15

Except performing reaction at 150° C. for 10 h instead of at 80° C. for 5 h at step b), then the catalyst was prepared following the precipitation route described in Example 1. The catalyst of this example is marked Cat-O. Via XRF, it contains 15.5% NiO, 17.8% ZnO, 11.0% $MoO_3$, 17.4% $WO_3$, 5.2% $Al_2O_3$, 3.0% $TiO_2$, 3.0% $K_2O$ and 26.0% $SiO_2$—$Al_2O_3$.

Comparative Example 1

According to example 2 in CN101619236A, the catalyst R1 was prepared. Via XRF, it contains 3.4% NiO, 16.6% $MoO_3$ and 80% $Al_2O_3$.

Comparative Example 2

According to example 3 in CN1317366C, the catalyst R2 was prepared. Via XRF, it contains 5.5% NiO, 10.5% $MoO_3$, 4.1% $K_2O$ and 79.9% $Al_2O_3$.

Comparative Example 3

According to example 1 in U.S. Pat. No. 6,299,760, the catalyst R3 was prepared. Via XRF, it contains 28.5% NiO, 27.5% $MoO_3$ and 44.0% $WO_3$.

Comparative Example 4

According to example 1 in CN101733120A, the catalyst R4 was prepared. Via XRF, it contains 36.1% NiO, 17.4% $MoO_3$, 28.1% $WO_3$ and 18.4% $Cr_2O_3$.

Example 16

Evaluation of catalyst performance during the selective hydrogenation of diolefin reaction of FCC gasoline:

The selective hydrogenation of diolefin reaction of FCC gasoline was carried out over catalysts in this invention, and the properties of feedstock are displayed in Table 1. For the catalytic tests, 10 mL of the catalyst (with a size of 20-30 mesh) was filled into 20 mL of fixed-bed reactor. Before reaction, it needs sulfidation in-situ using straight run gasoline containing 2 wt % $CS_2$, and the sulfidation condition (9 h, 290° C., a hydrogen pressure of 1.6 Mpa, an LHSV of 2.0 $h^{-1}$ and an $H_2$/oil ratio of 300 $Nm^3/m^3$) is the same with that of the contrast example 1 and 2. During removing diolefin, the reaction conditions include 80° C., a hydrogen pressure of 1.0 Mpa, an LHSV of 2.0 $h^{-1}$ and an $H_2$/oil ratio of 50 $Nm^3/m^3$. After 500 h, liquid samples were collected and analyzed as listed in Table 2.

Using maleic anhydride to measure the diene value in FCC gasoline as described as follows: 1) 10.00 g gasoline, 20 mL solution of maleic anhydride in toluene, and 0.5 mL 0.1M solution of $I_2$ in toluene were added into a flask in turn (before using, the solution of maleic anhydride in toluene must be filtered after stewing for overnight), shaking well. 2) Keep refluxing at 110° C.±2° C. for 3 h using water bath and a ground flask, at r.t. add 5 mL of water, and continue refluxing at 110° C.±2° C. for 15 min. When it cools to r.t., use 5 mL of MTBE and 20 mL of water to wash the condenser pipe. 3) Transfer the liquid in the ground flask to a separating funnel, and wash the flask wall three times with 20 mL of MTBE and 25 mL of water, respectively (While performing, it is necessary to guarantee the separating funnel is sealed without leaking for the sake of accuracy). 4) Shake the separating funnel for 4-5 min to separate water and oil. Collect the separated oil and add 25 mL, 10 mL and 10 mL of water respectively, to the oil for extraction, and collect the water into a conical flask. 5) In the conical flask, 1-2 drop of phenothalin is dropwised, using NaOH solution to titrate the water to neutral condition, and recording the consumed volume of NaOH solution. 6) Use 10.00 g toluene instead of the oil for a blank test. 7) Parallel samples, monitor and analyze the parallelism of the results 8) Calculate results (diene value unit, g $I_2$/100 g oil) as listed in equation 1:

$$\text{Diene value} = (B-A)(M)(12.69)/W \quad (1)$$

In equation 1, A refers to the consumed volume of NaOH solution (mL) by sample, B refers to the consumed volume of NaOH solution (mL) by the blank test sample, M refers to the concentration of NaOH solution (mol/L) and W refers to the weight of sample (g).

From results in Table 2, it can be found that the catalysts in this invention could still remove diolefin to less than 0.1 $gI_2$/100 g oil under mild conditions after 500 h operating in comparison with the reference catalyst, which could only reduce diolefin to about 0.5 $gI_2$/100 oil under the same conditions. The results show that the catalysts in this invention exhibit higher diolefin removal activity and stability than the contrast catalysts.

Compared to the present catalysts, the catalysts in this invention not only exhibit high activity and selectivity to diolefin, also lower the reaction temperature at least 50° C. in comparison with the conventional alumina supported catalysts. Furthermore, the catalysts in this invention possess strong S and As anti-poisoning and strong anti-coking ability, and a long operating cycle.

TABLE 1

The properties of FCC gasoline

| Properties | Results | Test method |
| --- | --- | --- |
| Density (20° C.), $kg/m^3$ | 720.8 | GB/T1884 |
| Procedure | | GB/T6536 |
| Initial boiling point, ° C. | 34.8 | |
| 10% | 51.3 | |
| 50% | 93.4 | |
| 90% | 163.2 | |
| The end point, ° C. | 191.1 | |
| Residue, % | 1.0 | |
| Sulfur content (ppm) | 62.2 | UV-Fluorescence |
| Diene value ($gI_2$/100 g oil) | 0.72 | Maleic anhydride method |
| Olefins, % | 26.5 | PONA |

TABLE 2

Performance of catalysts during the selective hydrogenation of dienes

| Catalysts | Surface area ($m^2/g$), volume (ml/g) | Diene value in products ($gI_2$/100 oil) |
| --- | --- | --- |
| Cat-A | 200, 0.43 | <0.1 |
| Cat-B | 185, 0.41 | <0.1 |
| Cat-C | 225, 0.47 | <0.1 |
| Cat-D | 182, 0.41 | <0.1 |
| Cat-E | 186, 0.44 | <0.1 |
| Cat-F | 184, 0.41 | <0.1 |
| Cat-G | 182, 0.41 | <0.1 |
| Cat-H | 200, 0.43 | <0.1 |
| Cat-I | 200, 0.43 | <0.1 |
| Cat-J | 200, 0.43 | <0.1 |
| Cat-K | 200, 0.43 | <0.1 |
| Cat-L | 200, 0.43 | <0.1 |
| Cat-M | 200, 0.43 | <0.1 |
| Cat-N | 200, 0.43 | <0.1 |
| Cat-O | 200, 0.43 | <0.1 |
| R1 | 254, 0.54 | 0.56 |
| R2 | 258, 0.56 | 0.58 |
| R3 | 105, 0.13 | 0.60 |
| R4 | 108, 0.16 | 0.56 |

We claim:

1. A catalyst for selective hydrogenation of dienes comprising a trivalent metal oxide, a Group IA metal oxide, a Group IIB metal oxide, a Group IVB metal oxide, a Group VIII metal oxide, at least two Group VIB metal oxides and an amount of $SiO_2$—$Al_2O_3$, wherein:
   $SiO_2$ is about 90-99 wt % in the $SiO_2$—$Al_2O_3$;
   said catalyst comprises 10-40 wt % of Group VIII oxide(s), 5-30 wt % of trivalent oxide(s), 0.1-8 wt % of Group IA metal oxide(s), 0.1-8 wt % of Group IVB metal oxide(s), 0.1-30 wt % of Group BB metal oxide(s), 5-50 wt % of Group VIB metal oxides, and 10-30 wt % of $SiO_2$—$Al_2O_3$;
   the molar ratio of the two Group VIB metal oxides is in the range of from 3:1 to 1:3;
   the surface area of the catalyst is 150-300 $m^2/g$; and
   the pore volume of the catalyst is 0.4-0.8 ml/g.

2. The catalyst of claim 1, wherein the trivalent metal oxide is Cr oxide or Al oxide; the Group IA metal oxide is Na oxide or K oxide; the Group IVB metal oxide is Ti oxide or Zr oxide; the Group IIB metal oxide is Zn oxide; the Group VIII metal oxide is nickel oxide or cobalt oxide, and the two Group VIB metal oxides are molybdenum oxide and tungsten oxide.

3. The catalyst of claim 1, wherein the two Group VIB metal oxides are Mo oxide and W oxide, the Group BB metal oxide is Zn oxide, the Group IA metal oxide is K oxide, the Group IVB metal oxide is Ti oxide, the Group VIII metal oxide is Ni oxide, and the trivalent metal oxide is Al oxide.

4. A method of preparation of the catalyst of claim 1, comprising the following steps:
 a) mixing a Group VIII metal soluble salt, a Group IIB metal soluble salt and a trivalent metal soluble salt, and then dissolving in water, adding aqueous solution of basic precipitant containing a Group IA metal to the mixed solution containing the above soluble salts to form a catalyst precipitate, then a layered double hydroxide catalyst precursor was obtained;
 b) combining the slurry of said layered double hydroxide catalyst precursor and a polar solvent containing at least two Group VIB metals soluble salts together for ion-exchanged reaction, filtering the catalyst precursor, washing, drying and calcining catalyst precursor at 400-500° C. for 2-10 h, and a mixture of metal oxides comprising the Group VIII metal oxide, the trivalent metal oxide, the Group IA metal oxide, the Group IIB metal oxide, and the at least two Group VIB metal oxides is obtained;
 c) grinding the mixture of the metal oxides of step b) into powder with a size at least lager than 100 mesh, mixing the powder with a binder containing Group IVB metal oxides and a mixture of $SiO_2$ and/or $Al_2O_3$ together for kneading, and extrusion molding; drying and calcinations at 400-500° C. for 2-10 h to obtain the catalyst of claim 1.

5. The method of claim 4, wherein the concentration of solution of the Group VIII metal soluble salt lies in the range of from 0.01 to 0.3 M, the concentration of solution of the trivalent metal soluble salt lies in the range of from 0.01 to 0.3 M, the concentration of solution of the Group IIB metal soluble salt lies in the range of from 0.01 to 0.3 M, the concentration of aqueous solution of basic precipitant containing of the Group IA metal soluble salt lies in the range of from 0.1 to 1.5 M, the concentration of the layered double hydroxide catalyst precursor is in the range of from 0.01 to 0.9 M, and the concentration of the at least two Group VIB metal soluble salts dissolved in the polar solvent is in the range of from 0.01 to 0.2 M.

6. The method of claim 4, wherein the precipitation reaction temperature in step a) is in the range of from 50 to 150° C. for 10 to 25 h; the ion-exchanged reaction temperature in step b) is in the range of from 50 to 150° C. for 4 to 10 h; the pH of ion-exchanged reaction system in step b) is in the range of from 1 to 11.

7. The method of claim 4, wherein said basic precipitant in step a) is selected from the group consisting of sodium hydroxide, potassium hydroxide, sodium carbonate, potassium carbonate, and mixtures of any two or more thereof.

8. The method of claim 4, wherein the Group VIII metal soluble salt is selected from the group consisting of nickel nitrate, nickel acetate, nickel sulfate, and nickel chloride; said trivalent metal soluble salt is selected from the group consisting of aluminium nitrate, aluminium acetate, aluminium chloride, chromium nitrate, chromium acetate, chromium chloride, cobalt nitrate, and cobalt chloride; said mixture of the at least two Group VIB metal soluble salts comprise one selected from the group consisting of ammonium molybdate and sodium molybdate and the other selected from the group consisting of ammonium tungstate, ammonium meta-tungstate, and sodium tungstate.

9. A method of removing a diolefin comprising conducting a selective hydrogenation of diolefin reaction in the presence of the catalyst of claim 1.

10. The method of claim 9, wherein the selective hydrogenation of diolefin reaction] is carried out at a temperature in the range of from 30 to 220° C., a hydrogen partial pressure in the range of from 0.1 to 10 MPa, a $H_2$/oil ratio in the range of from 10 to 300 $Nm^3/m^3$, and a liquid hourly space velocity in the range of from 0.1 to 10 $h^{-1}$.

11. The method of claim 9 further comprising pretreating the catalyst before conducting the selective hydrogenation of diolefin reaction as follows:
 a) calcining under air atmosphere at temperature from 350 to 550° C.;
 b) grinding, kneading, and extrusion molding;
 c) in a fixed-bed reactor, carrying out sulfidation in-situ using a mixture of a sulfur containing material and hydrogen at temperature in the range of from 250 to 400° C.;
 the sulfur containing material is selected from the group consisting of hydrogen sulfide, carbon disulfide, dimethyl disulfide, and combinations thereof, and the volume content of the sulfur containing material is 1-15% in the mixture of the sulfur containing material and hydrogen.

12. The method of claim 9, wherein the diolefin is a mixture of C4-C8 conjugated dienes.

13. The method of claim 9 wherein the diolefin is present in a gasoline.

* * * * *